(12) United States Patent
Hesselbarth (10) Patent No.: US 9,643,720 B2
(45) Date of Patent: May 9, 2017

(54) VERTICAL-TAKEOFF AIRCRAFT

(71) Applicant: Jonathan Hesselbarth, Darmstadt (DE)

(72) Inventor: Jonathan Hesselbarth, Darmstadt (DE)

( * ) Notice: Subject to any disclaimer, the term of this patent is extended or adjusted under 35 U.S.C. 154(b) by 0 days.

(21) Appl. No.: 14/416,760

(22) PCT Filed: Jul. 19, 2013

(86) PCT No.: PCT/EP2013/065361
§ 371 (c)(1),
(2) Date: Jan. 23, 2015

(87) PCT Pub. No.: WO2014/016226
PCT Pub. Date: Jan. 30, 2014

(65) Prior Publication Data
US 2015/0175260 A1  Jun. 25, 2015

(30) Foreign Application Priority Data
Jul. 27, 2012  (DE) ........................ 10 2012 106 869

(51) Int. Cl.
*B64C 29/00* (2006.01)
*B64C 11/46* (2006.01)
*B64D 27/26* (2006.01)

(52) U.S. Cl.
CPC .......... *B64C 29/0033* (2013.01); *B64C 11/46* (2013.01); *B64C 29/0075* (2013.01); *B64D 27/26* (2013.01)

(58) Field of Classification Search
CPC . B64C 29/0033; B64C 29/0075; B64C 11/46; B64D 27/26
See application file for complete search history.

(56) References Cited

U.S. PATENT DOCUMENTS 3,089,666 A * 5/1963 Quenzler .................. B64C 9/24
244/211
3,231,221 A * 1/1966 Platt .................... B64C 29/0033
244/12.4

(Continued)

FOREIGN PATENT DOCUMENTS

| GB | 2376928 A | 12/2002 |
| WO | 2012141738 A1 | 10/2012 |

OTHER PUBLICATIONS

International Search Report (Nov. 25, 2013) for corresponding International App. PCT/EP2013/065361.

*Primary Examiner* — Justin Benedik
(74) *Attorney, Agent, or Firm* — WRB-IP LLP (57) ABSTRACT

A vertical-takeoff aircraft with a wing. A first drive unit and a second drive unit are swivellably mounted on the wing. The first drive unit and the second drive unit are arranged on the wing at a distance from a wing-end of the wing. A first distance between the first drive unit and a longitudinal axis of the aircraft is approximately equal to a second distance between the second drive unit and the longitudinal axis of the aircraft. The first drive unit and the second drive unit are swivellable into a horizontal flying position and a vertical flying position. In the horizontal flying position the first drive unit is arranged above a wing surface and the second drive unit below the wing surface on the wing. In the vertical flying position the first drive unit and the second drive unit are arranged in an approximately horizontal plane. The first drive unit and the second drive unit each have a swivel arm, wherein the swivel arms are swivellably mounted on the wing.

6 Claims, 6 Drawing Sheets

(56) References Cited

U.S. PATENT DOCUMENTS

| | | | | | |
|---|---|---|---|---|---|
| 3,469,803 | A | * | 9/1969 | Schmielau | B64C 29/0075 244/12.4 |
| 4,492,353 | A | * | 1/1985 | Phillips | B64C 29/0075 244/12.4 |
| 5,085,315 | A | * | 2/1992 | Sambell | B64C 27/30 244/17.25 |
| 8,342,441 | B2 | * | 1/2013 | Yoeli | B64C 27/20 244/12.1 |
| 8,602,348 | B2 | * | 12/2013 | Bryant | B64C 29/0033 244/12.4 |
| 8,733,690 | B2 | * | 5/2014 | Bevirt et al. | B64C 29/0033 244/12.4 |

\* cited by examiner

VERTICAL-TAKEOFF AIRCRAFT

BACKGROUND AND SUMMARY

The invention relates to a vertical-takeoff aircraft with a wing, wherein a first drive unit and a second drive unit are arranged mounted pivotably on the wing, wherein the first drive unit and the second drive unit are arranged on the wing at a distance from one end of the wing, wherein a first distance of the first drive unit from a longitudinal axis of the aircraft is approximately identical to a second distance of the second drive unit from the longitudinal axis of the aircraft, and wherein the first drive unit and the second drive unit are pivotable into a horizontal flying position and a vertical flying position.

Vertical-takeoff aircrafts are used, inter alia, as drones and in the military sphere. These aircrafts customarily have two wings arrange on opposite sides of a fuselage, wherein in each case two drive units are arranged mounted pivotably on the wings in supporting elements which are adapted to the particular intended use and are connected rigidly to the wings. Aircrafts in which a separate fuselage is not formed and the wing is formed from two wing halves formed symmetrically along the longitudinal axis are also known, wherein in each case two drive units are arranged mounted pivotably on the wing halves in supporting elements Which are adapted to the particular intended use and are connected rigidly to the wing halves.

The supporting elements can be, for example, nacelles, which are arranged below the wings and in which the drive units are arranged mounted pivotably one behind another in the flying direction. For takeoff and landing and when hovering, the drive units are pivoted into the vertical flying position, wherein a drive force provided by the drive units acts substantially vertically in the direction of the ground and thereby permits a vertical rising, dropping and hovering flying position. As soon as the aircraft has reached a cruising height, the drive units are pivoted into the horizontal flying position. In the horizontal flying position, the drive force provided by the drive units acts substantially horizontally counter to the flying direction. Since, in the case of vertical-takeoff aircrafts with in each case two drive units arranged in a nacelle, the drive units are arranged one behind the other in the flying direction in the nacelle, the flow from the drive unit arranged at the front in the flying direction approaches the drive unit arranged therebehind. As a result, the efficiency of the vertical-takeoff aircraft in the horizontal flying position drops with respect to an available rotor surface.

It is also known to provide separate supporting elements for the drive units on the wings, wherein one separate supporting element is arranged rigidly above the wing, and one separate supporting element is arranged rigidly below the wing, on the wing. In this manner, the flows from the drive units do not approach each other in the horizontal flying position, and therefore the efficiency in the horizontal flying position is improved. Since the drive units are arranged at different heights, the drive units have, however, different ground effects in the vicinity of the ground during vertical flying, wherein a lift emanating from the drive unit arranged lower is customarily greater than a lift from the drive unit arranged higher. The drive power of the drive units arranged at different heights therefore has to be constantly readjusted during vertical flying. This leads to an unsteady flying behavior during vertical flying.

It is therefore desirable to further develop the known vertical-takeoff aircraft in such a manner that the efficiency during horizontal flying is as good as possible and the flying behavior during vertical flying is as steady as possible.

According to an aspect of the invention in the horizontal flying position, the first drive unit is arranged above a wing surface, and the second drive unit is arranged below the wing surface, on the wing, and in that, in the vertical flying position, the first drive unit and the second drive unit are arranged in an approximately horizontal plane. In this manner, a uniform ground effect of the first and second drive unit is achieved in the vertical flying phase in the vicinity of the ground, and therefore a steadier flying behavior, in particular in the takeoff and landing phase, is achieved. In the horizontal flying position, the flows from the first drive unit and the second drive unit do not approach each other, and therefore they do not cause any losses in efficiency. The first drive unit and the second drive unit are intended to be arranged in a horizontal plane as far as possible in the vertical flying position. However, slight deviations from such an arrangement, which can be attributed, for example, to manufacturing tolerances, impair the flying behavior only slightly, if at all.

In an advantageous manner, it is provided that the first drive unit and the second drive unit each have a pivoting arm, wherein the pivoting arms are arranged mounted pivotably on the wing. A pivot axis of the drive units can thereby be predetermined in such to manner that the first and the second drive unit are arranged substantially in a horizontal plane in the vertical flying position and are arranged above and below the wing surface in a horizontal flying position. The pivoting arms are expediently arranged on the wing in such a manner that, in the vertical flying position, the first drive unit is located in front of the wing, and the second drive unit behind the wing, in the horizontal flying direction. The pivoting arms here can be designed and arranged on the wing in such a manner that, in the horizontal flying position, the first drive unit and the second drive unit are arranged substantially in a vertical plane below and above the wing. However, it is also possible that, in the horizontal flying position, the first drive unit and the second drive unit are arranged spaced apart from a vertical plane on the wing.

The flying behavior of the vertical -takeoff aircraft can be further improved in that a fuselage distance of the first drive unit and of the second drive unit from the longitudinal axis of the aircraft is smaller than a wing end distance of the first drive unit and of the second drive unit from a wing axis which runs through the wing end and is parallel to the longitudinal axis. The drive units are expediently arranged as close as possible to the fuselage. A smallest possible fuselage distance is limited, for example, by a diameter of a rotor of the first drive unit or of the second drive unit.

The entire load of the drive, units is expediently transmitted to the fuselage via one or more suitable spars arranged within the wing. A lighter wing design can be used by the drive units being arranged on the wings in the vicinity of the fuselage, since the load of the drive units has to be conducted only by a small part of the wing to the fuselage.

Owing to the arrangement of the drive units in front of and behind the wing, the latter can be extended and therefore an additional aspect ratio can be generated. As a result, an induced resistance of the wings during horizontal flying drops and the flying performances are improved.

Furthermore, by means of the arrangement of the drive units in the vicinity of the fuselage, the wing, design becomes stiffer overall, and therefore smaller bending vibrations occur in the wings and the supporting spars. As a result, in particular maneuverability in the vertical flying position is improved and a steadier flying behavior is achieved.

It is advantageously provided according to the invention that a pivoting device is arranged on the wing, and the first drive unit and the second drive unit are operatively connected to the pivoting device. By means of the joint use of the pivoting device for the first and the second drive unit, the wing weight can be further reduced and the flying behavior of the vertical-takeoff aircraft can be further improved.

In order to be able to control the vertical-takeoff aircraft in as simple a manner as possible and thereby to permit steadier flying behavior, it is advantageously provided according to the invention that a pivoting movement of the first drive unit and a pivoting movement of the second drive unit are coupled. In addition, by means of the coupling of the pivoting movement, complex individual drives for independent rotation of the drive units can be dispensed with and particularly cost-effective and light pivoting devices can be used.

In a particularly advantageous refinement of the vertical-takeoff aircraft according to the invention, it is provided that the first drive unit and the second drive unit form a drive device, and in that at least two drive devices are arranged spaced apart from each other on the wing. In order to increase redundancy, it can accordingly be provided that two or three drive devices are arranged on the wing. However, depending on requirements, it is also possible for more than three drive devices to be arranged on the wing.

A particularly cost-effective design and particularly good flying behavior are achieved according to the invention by the first drive unit and the second drive unit being propeller drives or impeller drives or jet engines. Propeller drives are expediently formed rigidly or with rotor blade adjustment.

BRIEF DESCRIPTION OF THE DRAWINGS

Further advantages and refinements of the vertical-takeoff aircraft are explained in more detail with reference to the exemplary embodiments which are illustrated in the drawing.

In the drawing.

DETAILED DESCRIPTION

Figure 1:
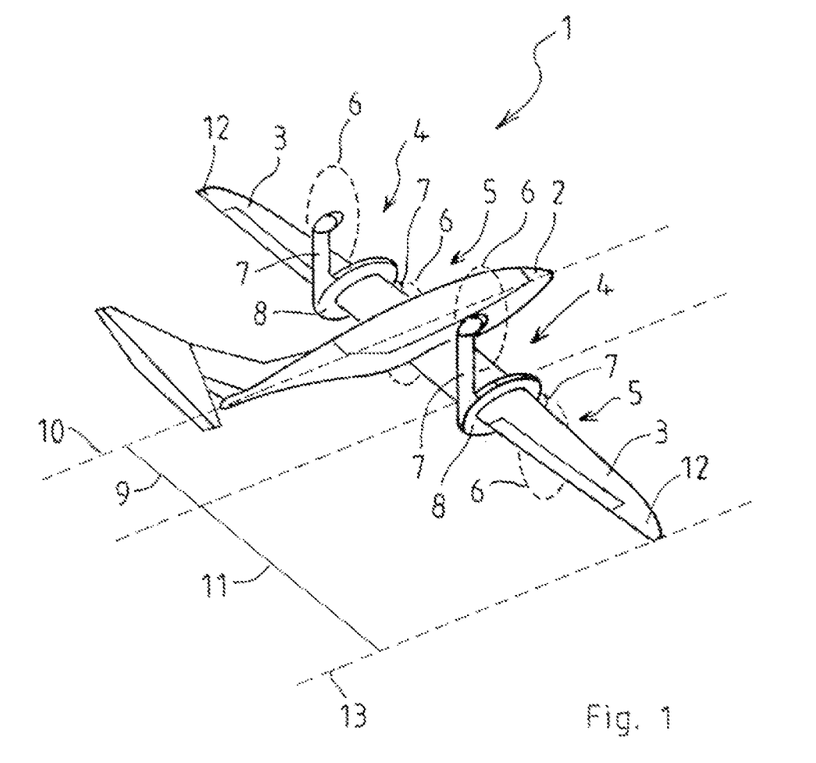
FIG. 1 shows a schematic illustration of a vertical-takeoff aircraft with wings arranged laterally on an aircraft fuselage during horizontal flying.
Figure 2:
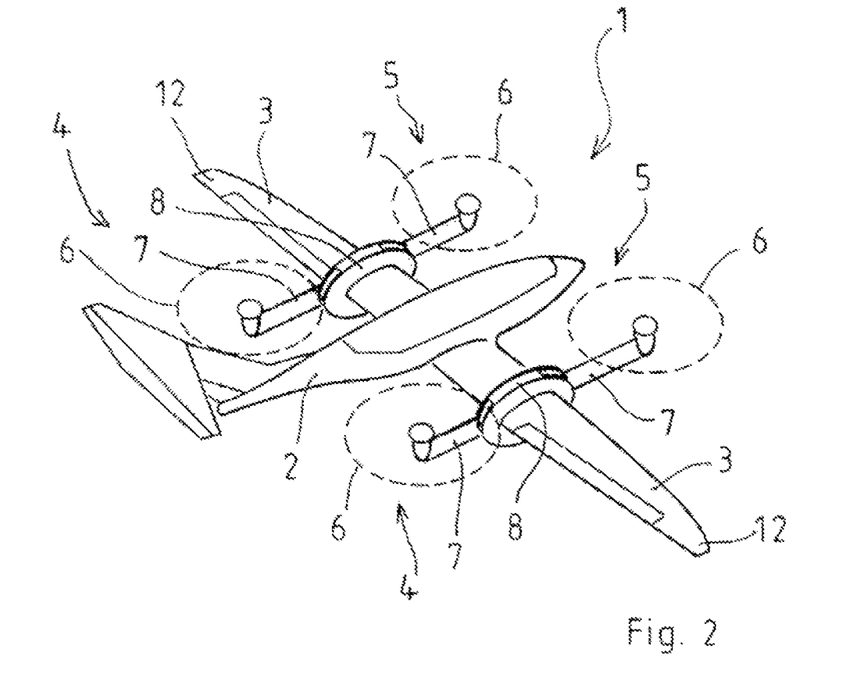
FIG. 2 shows a schematic illustration of a vertical-takeoff aircraft with wings arranged laterally on an aircraft fuselage during vertical flying.

FIGS. 1 and 2 show schematic illustrations of vertical-takeoff aircraft 1 with a wing 3 arranged in each case on opposite sides of a fuselage 2. A first drive unit 4 and a second drive unit 5 are in each case arranged mounted pivotably on the wings 3. The first drive unit 4 and the second drive unit 5 each have a propeller 6 and a pivoting arm 7. The pivoting arms 7 are arranged pivotably on the wings 3, wherein a coupled pivoting movement of pivoting devices 8 arranged on the wings 3 is triggered and driven.

The first drive unit 4 and the second drive unit 5 are arranged on the wings 3 in such a manner that a fuselage distance 9 of the drive units 4 and 5 from a longitudinal axis 10 of the vertical-takeoff aircraft 1 is smaller than a wing end distance 11 of the first drive unit 4 and of the second drive unit 5 from a wing axis 13 which runs through a wing end 12 and is parallel to the longitudinal axis 10.

In FIG. 1, the first drive unit 4 and the second drive unit 5 are in the horizontal flying position, whereas, in FIG. 2, the first drive unit 4 and the second drive unit 5 are illustrated in the vertical flying position.

Figure 3:
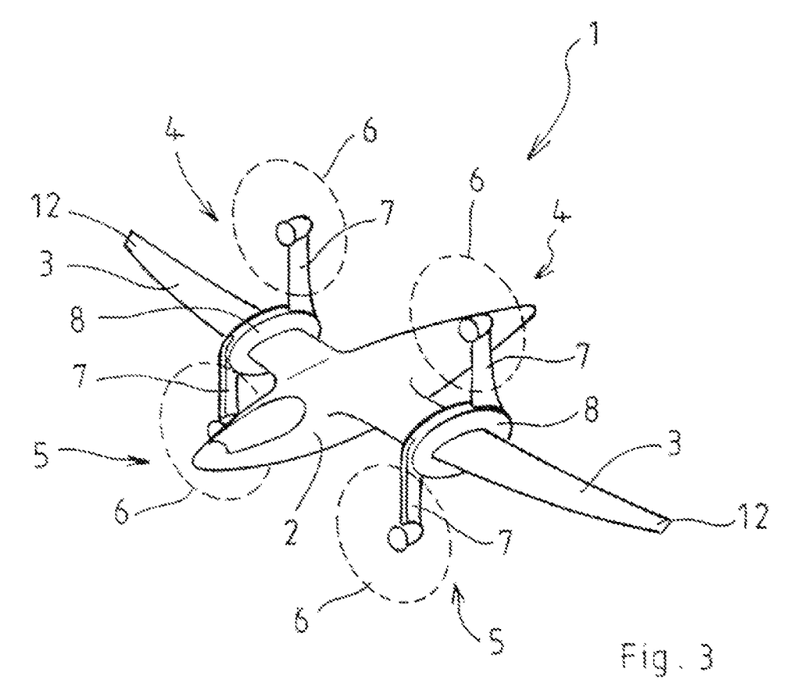
FIG. 3 shows a schematic illustration of a vertical-takeoff aircraft without a tail unit during horizontal flying with wings arranged on an upper side of the fuselage.

FIG. 3 schematically illustrates a vertical-takeoff aircraft 1 without a tail unit with two wings 3 arranged on an upper side of a fuselage 2.

Figure 4A:
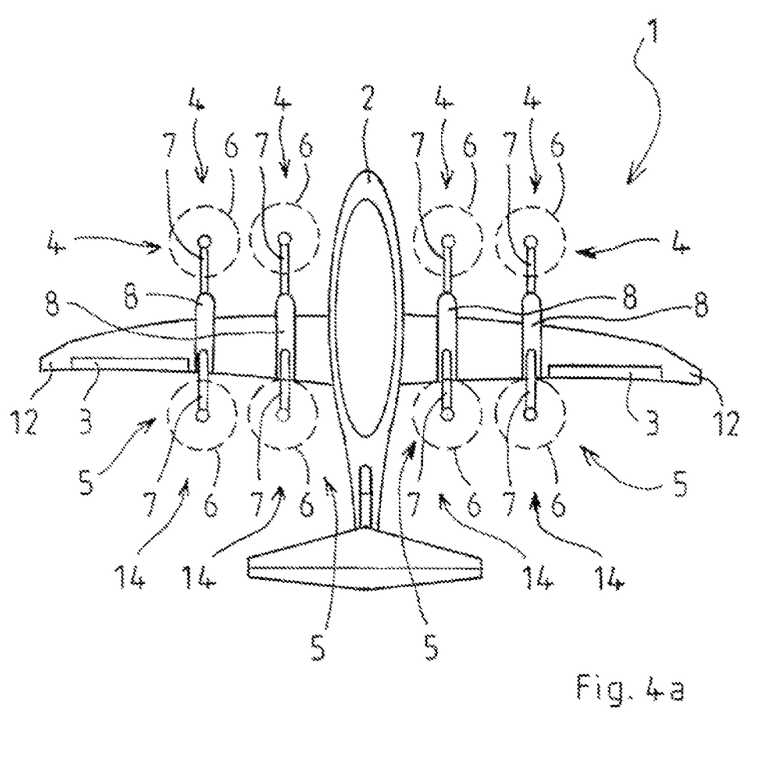
FIG. 4a shows a schematically illustrated top view of a vertical-takeoff aircraft during vertical flying with in each case two drive devices per wing.
Figure 4B:
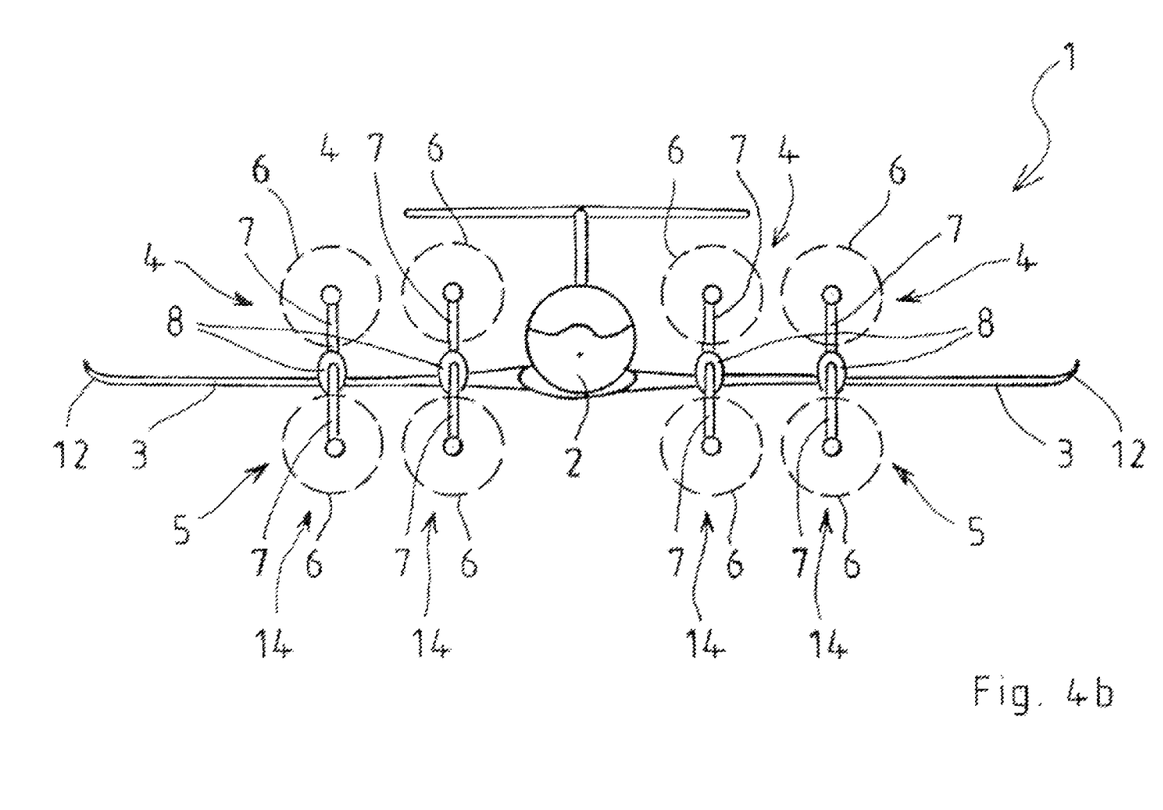
FIG. 4b shows a schematically illustrated front view of the vertical-takeoff aircraft illustrated in FIG. 4a during horizontal flying.

FIG. 4a shows a schematically illustrated top view, and FIG. 4b a schematically illustrated front view, of a vertical-takeoff aircraft 1 with two rings 3 arranged on opposite sides of the fuselage 2, wherein two drive devices 14 are arranged on each of the wings 3. The drive devices 14 in each case have a first drive unit 4 and a second drive unit. 5 which are arranged mounted pivotably on the wings 3 by means of pivoting arms.

The vertical-takeoff aircraft 1 is illustrated in the vertical flying phase in FIG. 4a. The drive units 4 and 5 are illustrated in the horizontal flying position in FIG. 4b.

Figure 5:
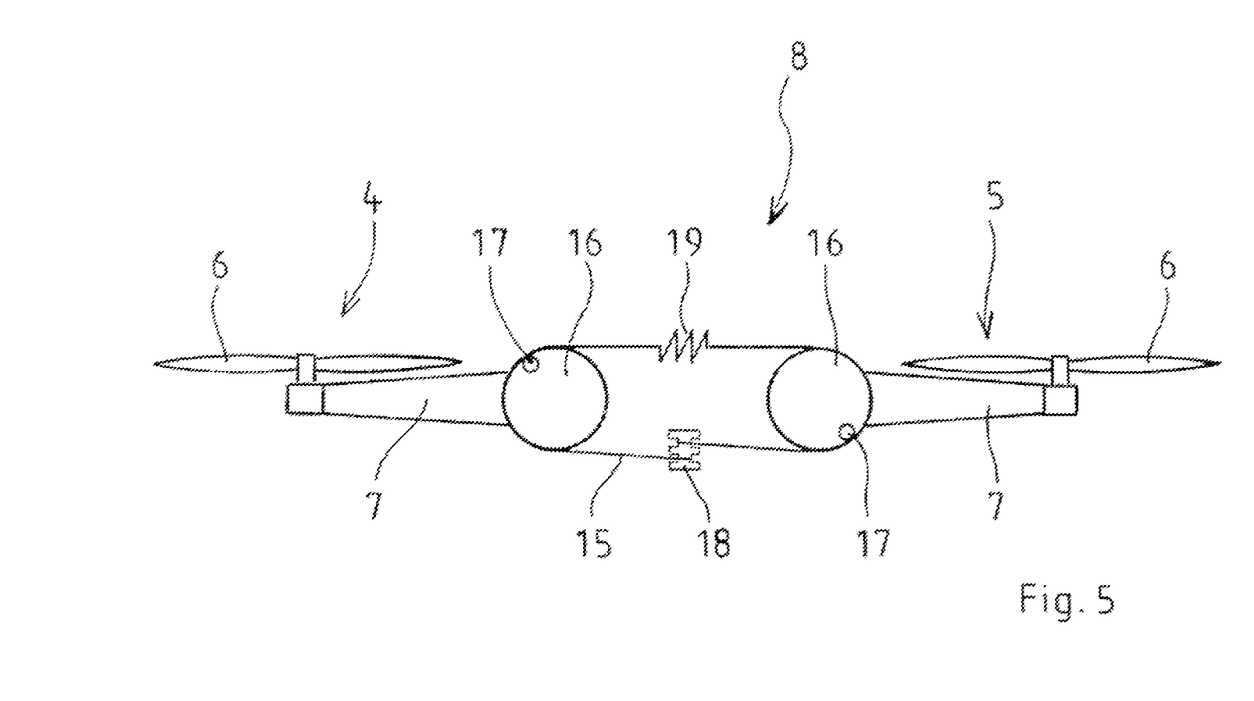
FIG. 5 shows a schematic illustration of a pivoting device with drive units arranged on the pivoting device.

FIG. 5 schematically illustrates a pivoting device 8 with two drive pulleys 16 driven via a drive belt 15. The drive belt 15 is in each case fixed to the drive pulleys 10 at fixing points 17. A position of the drive belt 15 can be adjusted via a winch 18. In order to install and remove the drive belt 15, a tensioning device 19 is provided on the drive belt 15.

A first drive unit 4 and a second drive unit 5 are arranged on the drive pulleys 16. The first drive unit 4 and the second drive unit 5 each have a pivoting arm 7 and a propeller 6 arranged on a pivoting arm 7.

By adjustment of the position of the drive belt 15 with the aid of the winch 18, the drive pulleys 16 are rotated in a coupled manner. In order to drive the winch 18, use can be made, for example, of an electric servo drive (not illustrated).

The invention claimed is:

1. A vertical-takeoff aircraft with a wing, the wing having an outermost end that is distal from a longitudinal axis of the aircraft, wherein a first drive unit and a second drive unit are arranged mounted pivotably on the wing, wherein the first drive unit and the second drive unit are arranged on the wing at a distance from the outermost end of the wing facing away from the longitudinal axis of the aircraft between the outermost end of the wing and the longitudinal axis, wherein a first distance of the first drive unit from the longitudinal axis of the aircraft is approximately identical to a second distance of the second drive unit from the longitudinal axis of the aircraft, and wherein the first drive unit and the second drive unit are pivotable into a horizontal flying position and a vertical flying position, wherein, in the horizontal flying position, the first drive unit is arranged above a wing surface on the wing, and the second drive unit is arranged below the wing, surface, and one of the first drive unit and the second drive unit is arranged longitudinally forward of the wing and the other of the first drive unit and the second drive unit is arranged longitudinally to a rear of the wing, and, in the vertical flying position, the first drive unit and the second drive unit are arranged in an approximately horizontal plane, wherein the first drive unit and the second drive unit each have a respective pivoting arm, wherein each pivoting arm is mounted on the wing.

2. The vertical-takeoff aircraft as claimed in claim 1, wherein a fuselage distance of the first drive unit and of the second drive unit from the longitudinal axis of the aircraft is smaller than a wing end distance of the first drive unit and of the second drive unit from a wing axis which runs through the wing end and is parallel to the longitudinal axis.

3. The vertical-takeoff aircraft as claimed in claim 1, wherein a pivoting device is arranged on the wing, and the first drive unit and the second drive unit are operatively connected to the pivoting device.

4. The vertical-takeoff aircraft as claimed in claim 1, wherein a pivoting movement of the first drive unit and a pivoting movement of the second drive unit are coupled.

5. The vertical-takeoff aircraft as claimed in claim 1, wherein the first drive unit and the second drive unit from a drive device, and in that at least two drive devices are arranged spaced apart from each other on the wing.

6. The vertical-takeoff aircraft as claimed in claim 1, wherein the first drive unit and the second drive unit are propeller drives or impeller drives or jet engines.

\* \* \* \* \*